United States Patent [19]

Casey et al.

[11] 4,224,513
[45] Sep. 23, 1980

[54] APPARATUS FOR THE ON-LINE MEASUREMENT OF THE OPACITY OF A PAPER SHEET

[75] Inventors: Joseph M. Casey, Santa Clara; Erik B. Dahlin, Saratoga, both of Calif.

[73] Assignee: Measurex Corporation, Cupertino, Calif.

[21] Appl. No.: 894,182

[22] Filed: Apr. 6, 1978

Related U.S. Application Data

[63] Continuation of Ser. No. 509,127, Sep. 25, 1974, abandoned, which is a continuation of Ser. No. 346,878, Apr. 2, 1973, abandoned.

[51] Int. Cl.$^2$ ............................................. H01J 3/14
[52] U.S. Cl. ................................. 250/216; 250/571; 356/432
[58] Field of Search ............... 356/201, 202, 432, 443, 356/444; 250/339, 562, 563, 572, 216

[56] References Cited

U.S. PATENT DOCUMENTS

| | | | |
|---|---|---|---|
| 2,474,828 | 7/1949 | Connelly et al. | 356/201 |
| 2,633,784 | 4/1953 | Cofield | 356/202 |
| 3,793,524 | 2/1974 | Howarth | 250/339 |

*Primary Examiner*—David C. Nelms
*Attorney, Agent, or Firm*—Flehr, Hohbach, Test, Albritton & Herbert

[57] ABSTRACT

A method of on-line control of opacity of moving sheet material being produced by a paper making machine includes an opacity control loop where an opacity additive is controlled and a basis weight control loop where the stock input to a headbox is controlled. These two control loops are decoupled by means of an opacity to stock feed forward and a basis weight to titanium dioxide feed forward. In addition, the effect of moisture change is decoupled from opacity. The opacity of the moving sheet material is measured by a system which employs a visible source and detector on opposite sides of the sheet. A diffusing window is placed both between the sheet and the source as well as between the sheet and the detector.

1 Claim, 3 Drawing Figures

OPACITY SENSOR OPTICAL SCHEMATIC

APPARATUS FOR THE ON-LINE MEASUREMENT OF THE OPACITY OF A PAPER SHEET

CROSS-REFERENCE TO RELATED APPLICATIONS

This application is a continuation of Ser. No. 509,127, filed Sept. 25, 1974, which application is a continuation of application Ser. No. 346,878, filed Apr. 2, 1973, (both now abandoned), both applications assigned to the present assignee.

BACKGROUND OF THE INVENTION

The present invention is directed to a method of on-line control of the opacity of a moving sheet material and more particularly to a method where the basis weight of the material varies and where an opacity additive also varies basis weight.

Previous on-line opacity control systems have found only limited use because the control of expensive additives on the basis of opacity measurement alone had not proved to be an efficient or profitable technique. Such control systems have been based on the premise of excellent basis weight control. Moreover, such methods have been unworkable for target shifts or grade changes since whenever basis weight would be changed it would cause a waste of expensive additives or the production of substandard sheet materials. In addition, the use of independent closed loop control systems for both opacity and basis weight tended to produce oscillations in such control loops after every change in opacity target or basis weight target. In order to reduce such oscillations one would typically tune the controllers for slow response which leads to lower quality of control for fast transients.

OBJECT AND SUMMARY OF THE INVENTION

It is, therefore, an object of the present invention to provide a process control method for on-line opacity control which decouples the effects of basis weight and opacity control.

In accordance with the above object there is provided a method of on-line control of the opacity of a moving sheet material which varies in basis weight where an opacity additive also varies basis weight as well as opacity. The basis weight of the sheet material is sensed and compared to a basis weight target to produce an error signal. The manipulated variable which determines the basis weight is adjusted to minimize the error signal. The opacity of the sheet material is sensed and compared to an opacity target to produce an error signal. The manipulated variable which determines the opacity is adjusted to minimize the error signal. The basis weight error signal is fed forward to the manipulated variable of opacity to hold the variable constant while the basis weight is being changed.

DETAILED DESCRIPTION OF THE PREFERRED EMBODIMENT

Figure 1:
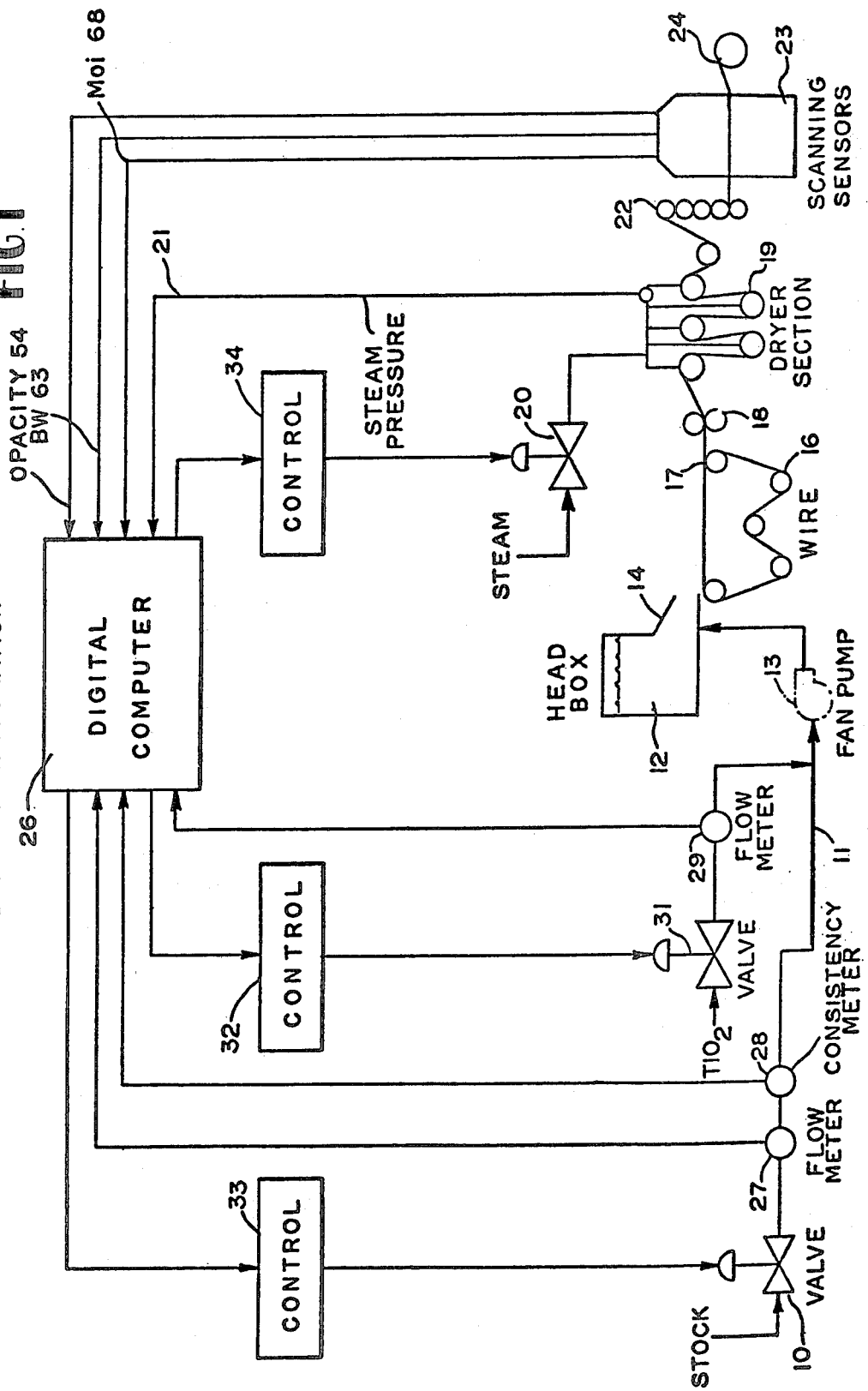
FIG. 1 is a simplified block diagram of a paper making machine including the associated control hardware embodying the present invention.

FIG. 1 illustrates a typical paper making machine which includes an associated control hardware configuration. Raw paper stock is supplied to the machine via a stock valve 10 and stock line 11 to a headbox 12 by a fan pump 13. The pulp and water mixture jets from headbox 12 through a slice 14 on top and parallel to wire 16. This forms a wet web 17. On leaving wire 16, web 17 passes through rollers 18 which remove much of the water from the web and essentially converts it to a sheet of wet paper. Thereafter, the paper sheet passes through a dryer section 19 consisting of several rollers through which steam is supplied by a steam control valve 20. The steam heats the rollers and consequently evaporates much of the water in the paper sheet so that the paper emerging from the dryer section 19 has the desired moisture content. Thereafter, the paper passes through a calender stack 22, through scanning sensors 23, and is wound on a reel 24.

Scanning sensors 23 provide measurement of opacity, basis weight and moisture all of which are coupled to a digital computer 26. Other control information coupled to the digital computer include stock line flow information from flow meter 27 and information from consistency meter 28. The flow of a titanium dioxide additive to control opacity which is added at the fan pump 13 is measured by a flow meter 29 and controlled by valve 31. Direct digital control units 32 and 33 control the titanium dioxide valve 31 and the stock valve 10 respectively. These two control units are coupled to digital computer 26.

Although in the present embodiment the titanium dioxide slurry is shown as being added at the fan pump 13 it could be added ahead of the stock flow valve if desired. A magnetic flow transmitter provides the computer with information on slurry flow by means of flow meter 29.

In addition to the control loops for opacity and basis weight where the titanium dioxide additive and stock flow are respectively controlled, a moisture control loop is provided by a direct digital control unit 34 which is coupled to digital computer 26 and controls the steam valve 20. Steam pressure is fed back to computer 26 on line 21.

Figure 2:
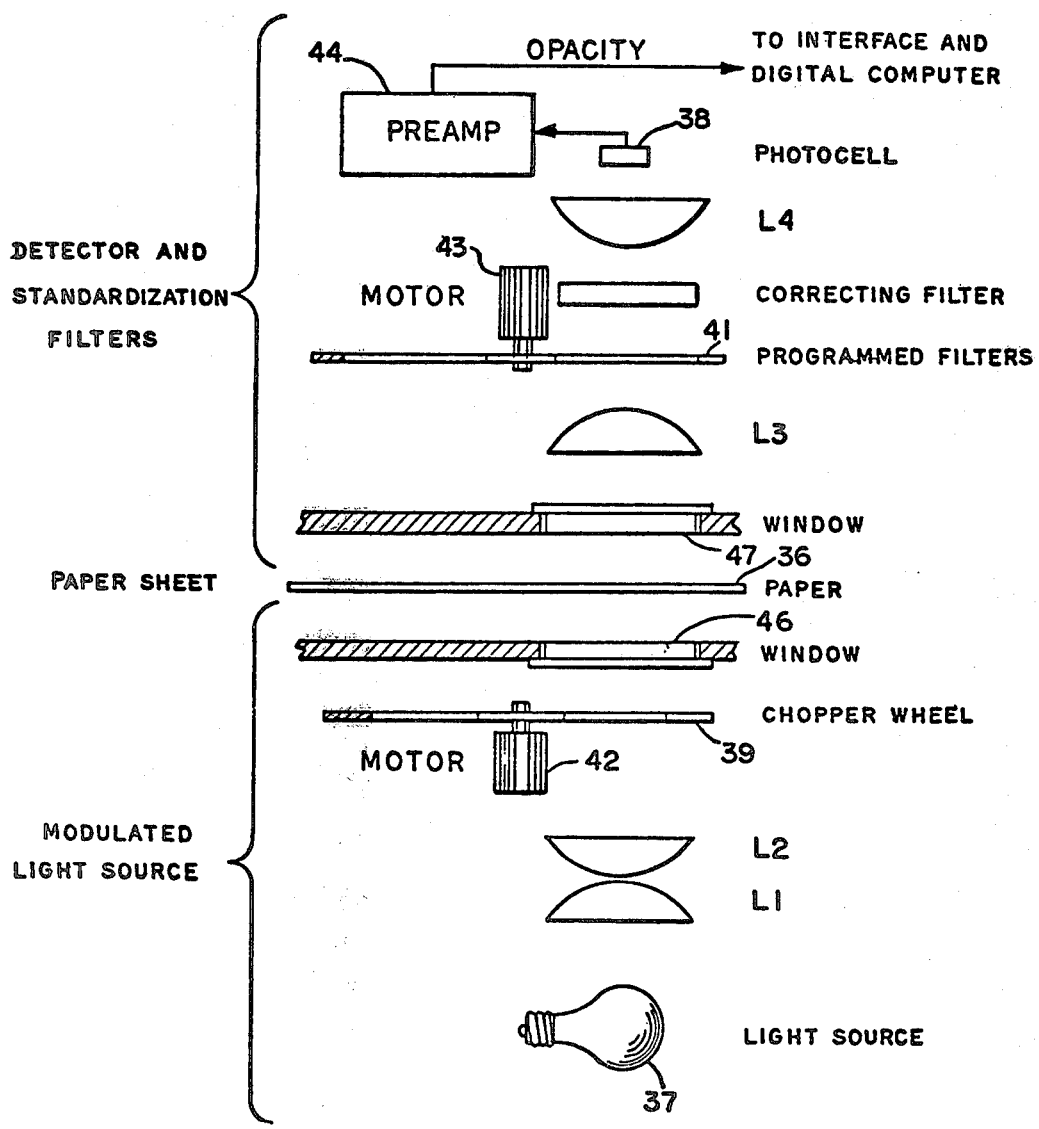
FIG. 2 is an optical schematic of the opacity sensor utilized in the present invention.

The opacity sensor illustrated in FIG. 2 measures the amount of light transmitted through the paper sheet 36. This is readily converted to a TAPPI standard opacity by a computer program. Typically, transmission of a material is a more sensitive measure of its opacity than its reflectance. A tungsten lamp 37 directs visible light through the paper sheet 36 and onto a solid state photocell or detector 38. The light is chopped by a chopper 39 before reaching paper 36 to produce an alternating signal at detector 38 which thus makes the signal independent of ambient light level. The detector spectral response matches that of the human eye and the light source is operated at the color temperature specified by TAPPI standard T425m-60. The lenses L, L2, L3 and L4 provide for a suitable optical path. In addition, the programmed filters 41 are utilized for periodic offsheet standardization. This compensates for any long term drift in the sensor. Both the chopper wheel 39 and programmed filters 41 are disks which are driven respectively by motors 42 and 43. The output of detector 38 is coupled to preamplifier 44 and provides an input signal to the digital computer 26 of FIG. 1. Windows are provided at 46 and 47 which are the diffusing type as disclosed and claimed in a U.S. Pat. No. 3,793,524, dated Feb. 19, 1974 entitled "Apparatus for Measuring a Characteristic of Sheet Materials," Ser. No. 286,053 filed Sept. 2, 1972, in the name of John J. Howarth and assigned to the present assignee.

In general, the digital computer 26 processes the opacity signal from the opacity sensor to convert such signal to the corresponding TAPPI opacity.

The light that is received by the silicon photocell 38 is converted to electrons. In general, in the electronics of the subsequent amplifier section (not shown in figure), the signal is divided into upper and lower channels. The upper channel is to adjust gain, filter and demodulate. The lower channel is used to provide a reference signal.

Figure 3:
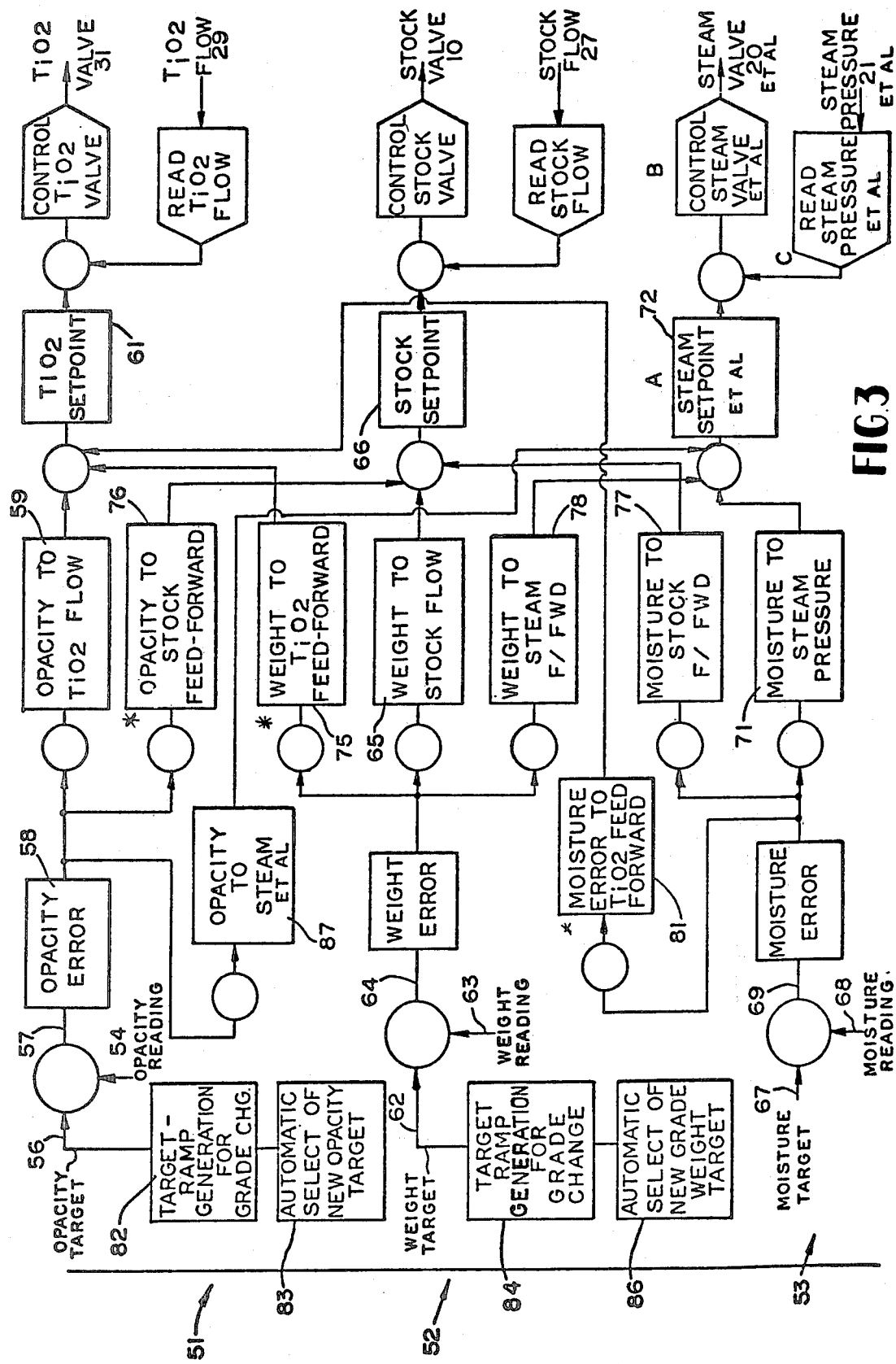
FIG. 3 is a block diagram of the control system embodying the present invention.

Referring now to FIG. 3, this control interaction block diagram shows the key control blocks required for decoupled control of basis weight, moisture and opacity. The decoupling of basis weight and moisture has been previously disclosed and claimed in U.S. Pat. No. 3,886,036 dated May 27, 1975, entitled "Method of Controlling a Drier Limited Paper Machine" in the name of Erik B. Dahlin, and assigned to the present assignee. As illustrated in the drawing, there are three basic control loops; namely, the opacity control loop 51, basis weight control loop 52 and the moisture control loop 53.

In the opacity control loop 52, the opacity reading appears on line 54 of the sensor of FIG. 2 and is compared to an opacity target signal on line 56 to produce an opacity error on line 57 which is processed in block 58. The opacity error is related to the flow of the titanium dioxide in block 59 to vary a titanium dioxide set point as illustrated by block 61. This setpoint then is coupled into the minor control loop which controls the titanium dioxide valve 31 and receives a measure of the titanium dioxide flow from flow meter 29. The circles represent the input points to the various control blocks.

The basis weight control loop 52 is similar and includes a weight target 62 which is compared to a basis weight reading 63 to produce a weight error on line 64 which is coupled to the weight to stock flow control unit 65 to control a stock setpoint 66. The stock setpoint 66 then controls the minor control loop which consists of stock valve 10 and the stock flow meter 27.

The moisture control loop 53 compares a moisture target 67 with a moisture reading 68 from the scanning sensors 23 as illustrated in FIG. 1 to produce a moisture error on line 69. This moisture error is coupled to the steam pressure control unit, block 71, which controls a steam setpoint at block 72. The output of the steam setpoint in block 72 controls the minor control loop which includes steam valve 20 and steam pressure measurement from line 21.

In accordance with the invention the key elements of the decoupled opacity control of the present invention are the blocks labeled weight to titanium dioxide feed forward, block 75, and opacity to stock feed forward block 76. The titanium dioxide feed forward block 75 is coupled to the titanium dioxide set point 61 and sends a signal to the set point which will exactly balance the opacity error signal that the current basis weight error will have caused. Thus, the titanium dioxide control set point will be unaffected by the basis weight error which will be handled solely by changing the stock flow setpoint at block 66. Thus, the opacity setpoint 61 will be held constant instead of being erroneously changed due to the opacity reading on line 54 reflecting a change in basis weight due to stock flow.

Similarly, opacity to stock feed forward block 76 provides a balancing of the basis weight error signal on line 64 which may be produced when the opacity target is changed or an opacity error signal in general is produced. In some cases, such feed forward or coupling of opacity to the stock setpoint 66 may not be necessary and merely the weight to titanium dioxide feed forward 75 to setpoint 61 could be successfully used in a practical embodiment.

A moisture to stock feed forward unit 77 is shown as coupled to stock setpoint 66 in order to decouple the effects of moisture change from the control of stock. Similarly a weight to steam feed forward, block 78, is coupled to steam setpoint 72.

All of the foregoing would, of course, actually be performed in digital computer 26.

In general, the effect of moisture change on opacity is very small. For example, a 1% moisture change would cause only approximately a 0.1% opacity change. However, moisture affects the total basis weight, while opacity is affected mainly by the dry basis weight (fiber weight). Thus weight changes due to moisture changes would cause erroneous feedforward signals if a "moisture to $TiO_2$ feedforward" were not included. In addition, decoupled control is required for dryer limited control and also grade change control. Accordingly, there is provided "moisture error to titanium dioxide feedforward" unit 81 which is coupled to the titanium dioxide setpoint 61. As an equivalent to the moisture decoupling performed by unit 81, the same effect can be achieved by decoupling opacity from dry basis weight. Of course, to obtain dry basis weight moisture must be determined. In addition, an "opacity to steam or master speed feed forward" block 87 doubles opacity error 58 to steam setpoint 72. In general, when the paper making machine is not on a grade change control, the opacity target and weight target are constant. They are manually entered from an operator station. However, during grade change control these targets are automatically change in small increments by the control computer at some predetermined rate or ramp. This is illustrated in FIG. 3 with target ramp generators. For example, the block 82 is coupled to the opacity target line 56 and is labeled "target ramp generation for grade change." This in turn is coupled to block 83 labeled "automatic select of new opacity target." Similarly, with respect to the weight target, a control unit block 84 provides "target ramp generation for grade change" and this in turn is coupled to block 86, "automatic select of new grade weight target." Thus, during gradge change, the control computer automatically retrieves the target for the opacity and basis weight from an operator entered specification of the grade named.

During grade change control and dryer limited control the output element with respect to moisture is the master speed of the paper machine and not the steam setpoint. Thus, the steam setpoint block 72 would in actuality be the "master speed setpoint," the steam valve 20 would instead be the "master speed rheostat" and the steam pressure feedback 21 would actually be the "rheostat position feedback."

To summarize, the present invention provides a control strategy which is based on the fact that a change in basis weight will cause a change in opacity, thus changing the amount of the opacity additive required to maintain a certain minimum target opacity; similarly a change in opacity additive flow will tend to change the amount of fiber or stock flow required to maintain a certain target basis weight. Thus, clearly the two variables interact in that a control move that changes the opacity additive flow will also change the final basis weight and similarly basis weight move will affect opacity. The present invention decouples the basis weight and opacity control loops so that basis weight target changes can be accomplished while holding opacity constant; in addition, basis weight excursions from target are remedied by stock flow changes only and expensive opacity additives such as titanium dioxide or clay are not used to remedy basis weight decreases. Effects of moisture change on basis weight are also decoupled or compensated for. Finally, the method of the present invention is ideally suited for grade changes in which during the ramping of the opacity target from an old to new grade the other manipulated variables of the process such as stock flow are effectively decoupled. This provides a fully automatic grade change.

We claim:
1. Apparatus for measuring the opacity of a moving sheet of paper or the like comprising: a visible light source; a visible light detector; means for supporting said light source and detector on opposite sides of said sheet; a first diffusing window between said source and said sheet; a second diffusing window between said detector and said sheet; and means for sensing the amount of light transmitted through said sheet and providing a signal related to opacity of the sheet.

* * * * *